(12) United States Patent
Wegner et al.

(10) Patent No.: US 7,465,597 B2
(45) Date of Patent: Dec. 16, 2008

(54) METHOD OF MANUFACTURING A DIAGNOSTIC TEST STRIP

(75) Inventors: Greta Wegner, Pompano Beach, FL (US); Natasha Popovich, Pompano Beach, FL (US)

(73) Assignee: Home Diagnostics, Inc., Fort Lauderdale, FL (US)

( * ) Notice: Subject to any disclaimer, the term of this patent is extended or adjusted under 35 U.S.C. 154(b) by 295 days.

(21) Appl. No.: 11/476,702

(22) Filed: Jun. 29, 2006

(65) Prior Publication Data

US 2008/0003709 A1 Jan. 3, 2008

(51) Int. Cl.
*H01L 21/00* (2006.01)

(52) U.S. Cl. .............................. 438/48; 438/1; 438/758; 257/E51.045

(58) Field of Classification Search ................... 438/48; 257/758; 204/603
See application file for complete search history.

(56) References Cited

U.S. PATENT DOCUMENTS

| | | | |
|---|---|---|---|
| 5,248,912 A | | 9/1993 | Zdeblick |
| 5,376,252 A | * | 12/1994 | Ekstrom et al. ............. 204/603 |
| 5,437,999 A | | 8/1995 | Diebold et al. |
| 5,466,575 A | | 11/1995 | Cozzette et al. |
| 5,694,932 A | | 12/1997 | Michel |
| 6,004,441 A | | 12/1999 | Fujiwara et al. |

(Continued)

FOREIGN PATENT DOCUMENTS

| EP | 1 787 717 A | 5/2007 |
|---|---|---|

(Continued)

OTHER PUBLICATIONS

T. Akai et al., "Fabrication Process of Fine Electrodes Using Shadow Mask Evaporation and Tip-Induced Local Oxidation," Japanese Journal of Applied Physics, Japan Society of Applied Physics, Tokyo, JP, vol. 41, No. 7B, Part 1, Jul. 2002, pp. 4883-4886, XP001163092, ISSN: 0021-4922, pp. 4884-4885.

(Continued)

*Primary Examiner*—Walter Lindsay, Jr.
*Assistant Examiner*—Abdulfattah Mustapha
(74) *Attorney, Agent, or Firm*—Finnegan, Henderson, Farabow, Garrett & Dunner, L.L.P (57) ABSTRACT

A method for manufacturing a biosensor is provided. The method may include positioning a shadow mask containing a pattern of a plurality of feature sets over a substantially planar base layer containing a plurality of registration points. The method may also include forming at least one of the plurality of feature sets on the substantially planar base layer by selectively depositing a layer of a conductive material on the substantially planar base layer by passing the conductive material through the pattern of the shadow mask and removing the shadow mask from the substantially planar base layer. Alternatively, the method may include providing a laminate structure including a substantially planar base layer containing a plurality of registration points and a photoresist layer containing a pattern of a plurality of feature sets. The method may further include forming at least one of the plurality of feature sets on the substantially planar base layer by selectively depositing a layer of a conductive material on the substantially planar base layer by passing the conductive material through the pattern of the photoresist layer and removing the photoresist layer from the substantially planar base layer.

19 Claims, 10 Drawing Sheets

U.S. PATENT DOCUMENTS

| | | |
|---|---|---|
| 6,306,594 B1 | 10/2001 | Cozzette et al. |
| 6,309,526 B1 | 10/2001 | Fujiwara et al. |
| 6,436,256 B1 | 8/2002 | Williams et al. |
| 6,540,890 B1 | 4/2003 | Bhullar et al. |
| 6,579,690 B1 | 6/2003 | Bonnecaze et al. |
| 6,638,722 B2 | 10/2003 | Douglas et al. |
| 6,645,359 B1 | 11/2003 | Bhullar et al. |
| 6,662,439 B1 | 12/2003 | Bhullar |
| 6,767,440 B1 | 7/2004 | Bhullar et al. |
| 6,805,780 B1 | 10/2004 | Ryu et al. |
| 6,855,243 B2 | 2/2005 | Khan |
| 6,875,327 B1 | 4/2005 | Miyazaki et al. |
| 6,897,135 B2 | 5/2005 | Izumi et al. |
| 6,905,614 B1 | 6/2005 | Novotny |
| 2002/0081501 A1 | 6/2002 | Hasegawa et al. |
| 2003/0018420 A1 | 1/2003 | Apanius et al. |
| 2003/0094367 A1 | 5/2003 | Bhullar et al. |
| 2003/0106810 A1 | 6/2003 | Douglas et al. |
| 2003/0150724 A1 | 8/2003 | Kawanaka et al. |
| 2003/0155237 A1* | 8/2003 | Surridge et al. ........ 204/403.14 |
| 2003/0221613 A1 | 12/2003 | Kang et al. |
| 2004/0026243 A1 | 2/2004 | Davies et al. |
| 2004/0084307 A1 | 5/2004 | Kim et al. |
| 2004/0163953 A1 | 8/2004 | Bhullar et al. |
| 2004/0178066 A1 | 9/2004 | Miyazaki et al. |
| 2004/0178067 A1 | 9/2004 | Miyazaki et al. |
| 2004/0182703 A1 | 9/2004 | Bell et al. |
| 2004/0194302 A1 | 10/2004 | Bhullar et al. |
| 2005/0045476 A1 | 3/2005 | Neel et al. |
| 2005/0103624 A1 | 5/2005 | Bhullar et al. |
| 2005/0128788 A1 | 6/2005 | Segal et al. |
| 2005/0161826 A1* | 7/2005 | Shah et al. .................. 257/758 |
| 2005/0250228 A1 | 11/2005 | Ko |

FOREIGN PATENT DOCUMENTS

WO    WO 2006/088425 A    8/2006

OTHER PUBLICATIONS

Saipeng Yang et al., "Microfabricated Glucose Biosensor with Glucose Oxidase Entrapped in Sol-Gel Matrix," Talanta, vol. 47, No. 3, Nov. 1998, pp. 735-743, XP002468331, ISSN: 0039-9140, pp. 737-738.

Invitation to Pay Additional Fees, dated Feb. 25, 2008 in PCT/US2007/071885.

* cited by examiner

METHOD OF MANUFACTURING A DIAGNOSTIC TEST STRIP

TECHNICAL FIELD

The present invention relates to the field of diagnostic testing and, more particularly, to diagnostic testing systems using electronic meters.

BACKGROUND

Electronic testing systems are commonly used to measure or identify one or more analytes in a sample. Such testing systems can be used to evaluate medical samples for diagnostic purposes and to test various non-medical samples. For example, medical diagnostic meters can provide information regarding the presence, amount, or concentration of various analytes in human or animal body fluids. In addition, diagnostic test meters can be used to monitor analytes or chemical parameters in non-medical samples such as water, soil, sewage, sand, air, beverage and food products or any other suitable sample.

Diagnostic testing systems typically include both test media, such as diagnostic test strips, and a test meter configured for use with the test media. Suitable test media may include a combination of electrical, chemical, and/or optical components configured to provide a response indicative of the presence or concentration of an analyte to be measured. For example, some glucose test strips include electrochemical components, such as glucose specific enzymes, buffers, and one or more electrodes. The glucose specific enzymes may react with glucose in a sample, thereby producing an electrical signal that can be measured with the one or more electrodes. The test meter can then convert the electrical signal into a glucose test result.

There is a demand for improved test media. For example, in the blood glucose testing market, consumers consistently insist on test media that require smaller sample sizes, thereby minimizing the amount of blood needed for frequent testing. Consumers also demand robust performance and accurate results, and will not tolerate erroneous tests due to inadequate sample size. In addition, in all diagnostic testing markets, consumers prefer faster, cheaper, more durable, and more reliable testing systems.

Current methods of manufacturing diagnostic test media have inherent limits. For example, current methods for producing test media electrodes and depositing enzymes or other chemicals may have limited spatial resolution and/or production speeds. Furthermore, some production processes cannot be used to deposit some enzymes, chemicals, and electrodes. In addition, some production processes may be used to produce or deposit some test media components, such as electrodes or enzymes, while being incompatible with other components. Therefore, some test media production processes may require multiple production techniques, thereby increasing production cost and time, and decreasing product throughput.

Several methods for manufacturing biosensors have been proposed. One such method is described in U.S. Pat. No. 6,875,327 to Miyazaki et al. Miyazaki et al. describe a biosensor manufacturing process whereby a conductive layer is formed on a support. Electrodes are formed using a laser to form multiple "slits" in the conductive layer, which form electrical separations between the working, counter and detecting electrodes. Following electrode formation, chemical reagents are selectively applied to the conductive layer.

U.S. Pat. No. 6,805,780 to Ryu et al. describes a method for producing electrochemical biosensor test strips. The process includes forming a groove in a first insulating substrate and sputtering a metal onto the insulating substrate with the aid of a shadow mask to form a pair of electrodes. The shadow mask should be in close contact with the substrate to avoid deposited material entering gaps and reducing the quality of the pattern formed. The shadow mask may be placed in contact with a substrate, or may be formed by cutting a pattern in a plastic layer adhered to the substrate, which is termed "adhesive-type shadow mask."

U.S. Published Application No. 2005/0161826 to Shah et al. describes a manufacturing method that utilizes shadow mask techniques and lift-off lithography. Lift-off lithography uses a photo-resist layer patterned to form a negative image of the conducting elements. A thin metal film is formed over the substrate by, for example, sputtering. Next, the photo-resist layer is removed by chemical stripping, leaving conductive elements formed by the metal that remains on the substrate. The shadow mask process is also used to form sacrificial structures on the substrate, and multiple layers of dielectric and conductor material may be formed using both processes. Initially a dielectric substrate base is formed, followed by patterning a blanket layer of conductive thin-film. Sacrificial structures may then be formed, using, shadow mask deposition. At least one dielectric layer is deposited on the multilayer circuit. Conductors and sacrificial structures may then be created and removed, forming multiple conductive and dielectric layers.

There exists the need to mass-produce biosensors cost effectively and with high precision. The prior art references have several limitations solved by the current invention. Although the electrode design described by Miyazaki et al. can provide a functional biosensor, improved methods of manufacturing biosensor electrodes are desirable. Specifically, other manufacturing methods may be used to lower the cost and/or increase the quality of electrode formation and biosensor performance. For example, steps described by Rye et al. may require the formation of a groove in the substrate, adding cost and complexity to biosensor manufacturing. Further, Rye et al. discloses the formation of a single test strip containing only two electrodes. Other limitations of the prior art include the fact that Shah et al. requires the application of at least one dielectric layer to form the multilayer circuit structure.

Accordingly, there is a need for improved methods of manufacturing diagnostic testing systems.

SUMMARY

A first aspect of the present invention includes a method for manufacturing a test strip. The method includes positioning a shadow mask containing a pattern of a plurality of feature sets over a substantially planar base layer containing a plurality of registration points. The method also includes forming at least one of the plurality of feature sets on the substantially planar base layer by selectively depositing a layer of a conductive material on the substantially planar base layer by passing the conductive material through the pattern of the shadow mask and removing the shadow mask from the substantially planar base layer.

A second aspect of the present invention includes a method for manufacturing a test strip. The method includes providing a laminate structure including a substantially planar base layer containing a plurality of registration points and a photoresist layer containing a pattern of a plurality of feature sets. The method also includes forming at least one of the plurality of feature sets on the substantially planar base layer by selectively depositing a layer of a conductive material on the substantially planar base layer by passing the conductive material through the pattern of the photoresist layer and removing the photoresist layer from the substantially planar base layer.

Additional aspects and advantages of the invention will be set forth in part in the description which follows, and in part will be apparent from the description, or can be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

In accordance with an exemplary embodiment, a biosensor manufacturing method is described. Many industries have a commercial need to monitor the concentration of particular constituents in a fluid. The oil refining industry, wineries, and the dairy industry are examples of industries where fluid testing is routine. In the health care field, people such as diabetics, for example, need to monitor various constituents within their bodily fluids using biosensors. A number of systems are available that allow people to test a body fluid (e.g. blood, urine, or saliva), to conveniently monitor the level of a particular fluid constituent, such as, for example, cholesterol, proteins or glucose.

A biosensor may include a test strip, which can be disposable, that may facilitate the detection of a particular constituent of a body fluid. The test strip can include a proximal end, a distal end, and at least one electrode. The proximal end of the test strip may include a sample chamber for receiving a body fluid to be tested. The sample chamber can be dimensioned and configured to draw a fluid sample into the sample chamber via capillary action. Electrodes positioned within the sample chamber may contact the fluid sample. The distal end of the test strip may be configured to operatively connect the test strip to a meter that may determine the concentration of the body fluid constituent. For example, the distal end of the test strip may include a plurality of electrical contacts configured to provide electrical connections between the electrodes within the sample chamber and the meter. The ends of the test strip may also include a visual and/or tactile distinguishable section, such as, for example, a taper, in order to make it easier for the user to operatively connect the test strip to the meter or apply a body fluid to the sample chamber.

Electrodes positioned within the sample chamber may include a working electrode, a counter electrode, and a fill-detect electrode. A reagent layer can be disposed in the sample chamber and may cover at least a portion of the working electrode, which can also be disposed at least partially in the sample chamber. The reagent layer can include, for example, an enzyme, such as glucose oxidase, and a mediator, such as potassium ferricyanide or ruthenium hexamine, to facilitate the detection of glucose in blood. It is contemplated that other reagents and/or other mediators can be used to facilitate detection of glucose and other constituents in blood and other body fluids. The reagent layer can also include other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485).

Figure 1A:
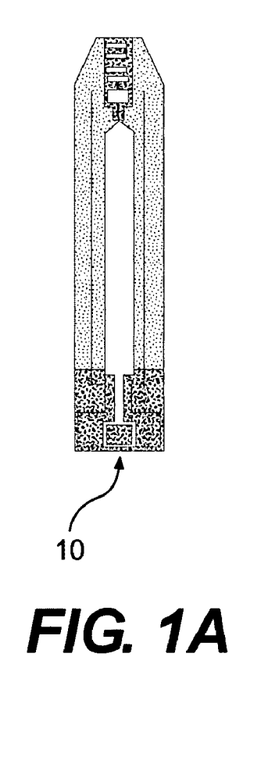
FIG. 1A illustrates test media that can be produced using the methods of the present disclosure.
Figure 1B:
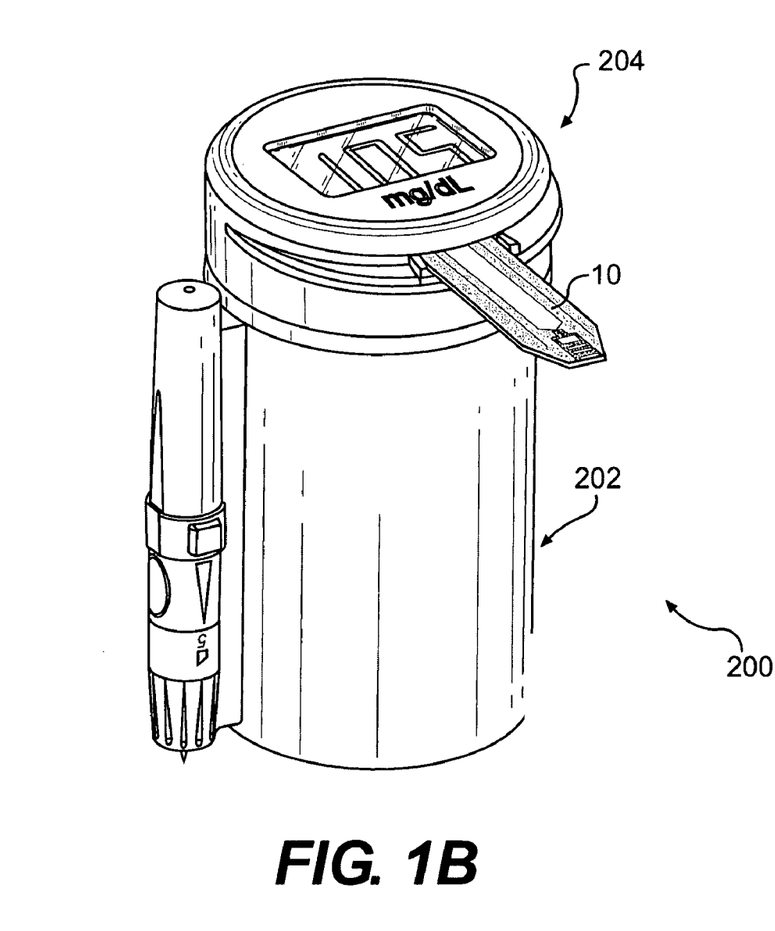
FIG. 1B illustrates a test meter that can be used with test media produced according to the methods of the present disclosure.
Figure 1C:
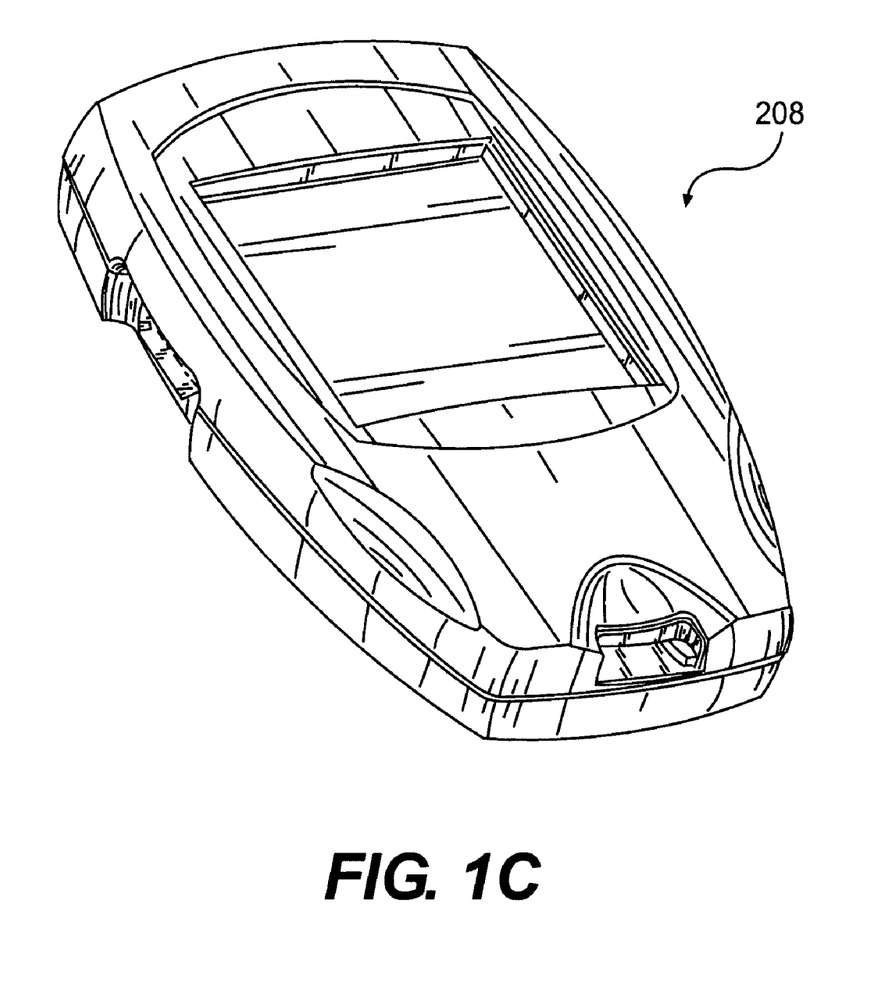
FIG. 1C illustrates a test meter that can be used with test media produced according to the methods of the present disclosure.

The present disclosure provides a method for producing a diagnostic test strip 10, as shown in FIG. 1A. Test strip 10 of the present disclosure may be used with a suitable test meter 200, 208, as shown in FIGS. 1B and 1C, to detect or measure the concentration of one or more analytes. The analytes to be tested for may include a variety of different substances, which may be found in biological samples, such as blood, urine, tear drops, semen, feces, gastric fluid, sweat, cerebrospinal fluid, saliva, vaginal fluids (including suspected amniotic fluid), culture media, and/or any other biologic sample. The one or more analytes may also include substances found in environmental samples such as soil, food products, ground water, pool water, and/or any other suitable sample.

As shown in FIG. 1A, test strip 10 are planar and elongated in design. However, test strip 10 may be provided in any suitable form including, for example, ribbons, tubes, tabs, discs, or any other suitable form. Furthermore, test strip 10 can be configured for use with a variety of suitable testing modalities, including electrochemical tests, photochemical tests, electro-chemiluminescent tests, and/or any other suitable testing modality.

Test meter 200, 208 may be selected from a variety of suitable test meter types. For example, as shown in FIG. 1B, test meter 200 includes a vial 202 configured to store one or more test strips 10. The operative components of test meter 200 may be contained in a meter cap 204. Meter cap 204 may contain electrical meter components, can be packaged with test meter 200, and can be configured to close and/or seal vial 202. Alternatively, a test meter 208 can include a monitor unit separated from storage vial, as shown in FIG. 1C. Any suitable test meter may be selected to provide a diagnostic test using test strip 10 produced according to the disclosed methods.

Test Strip Configuration

Figure 2A:
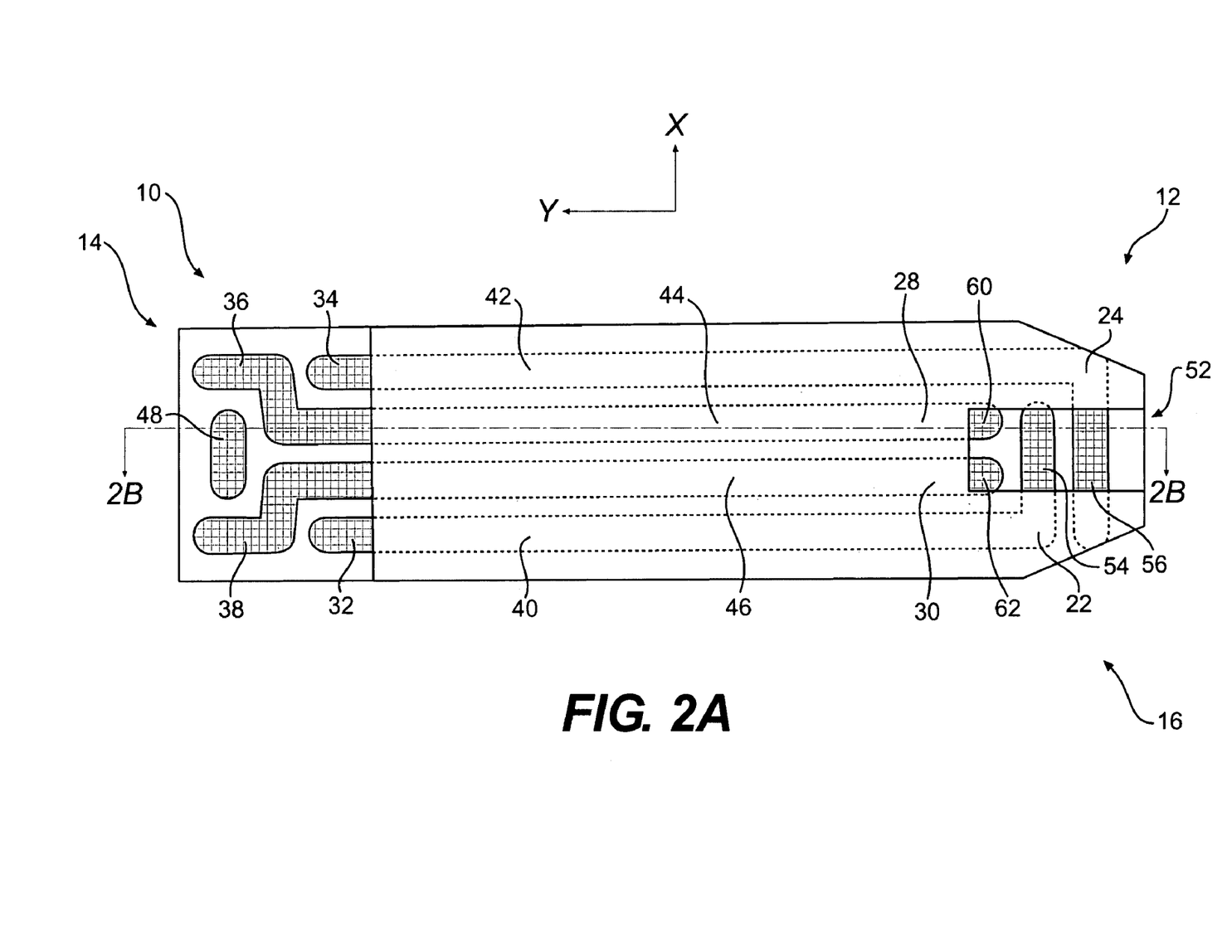
FIG. 2A is a top plan view of a test strip according to an exemplary embodiment of the invention.
Figure 2B:
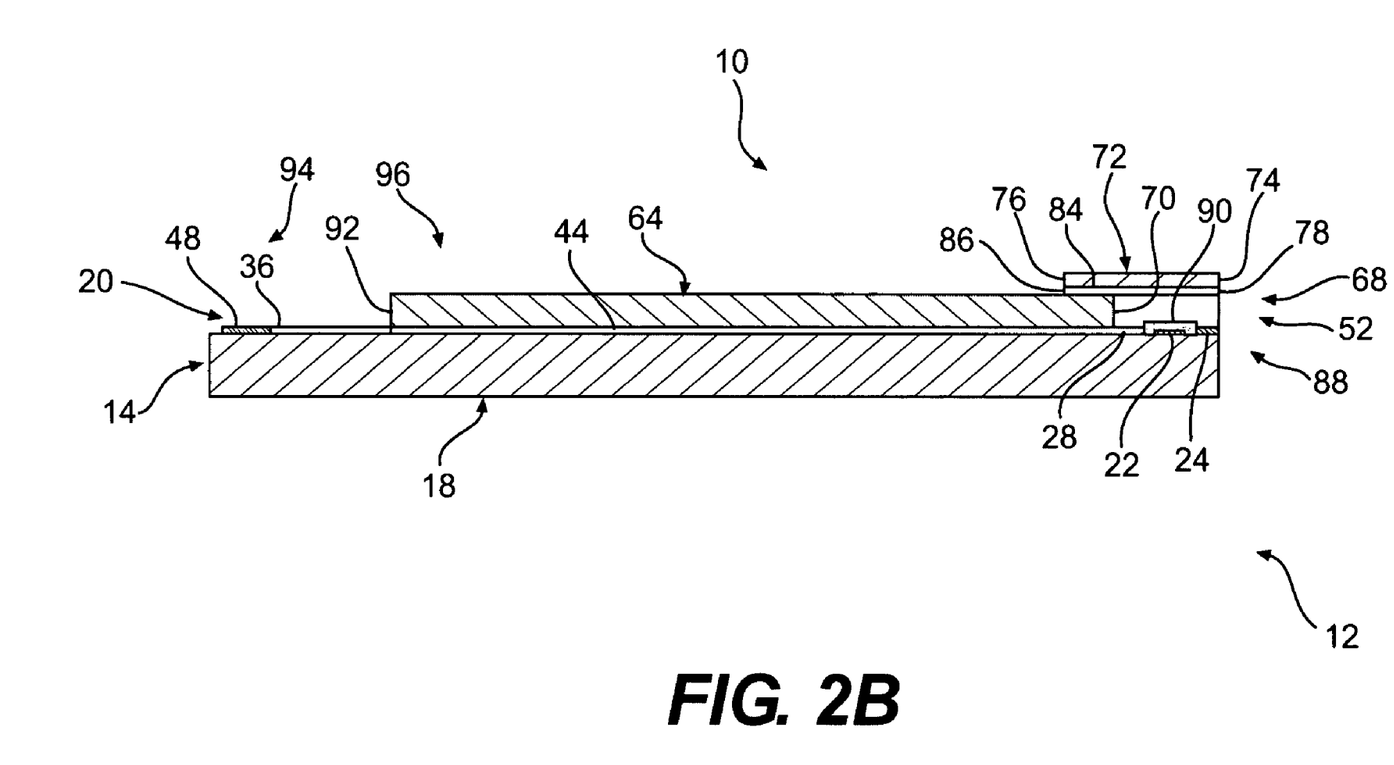
FIG. 2B is a cross-sectional view of the test strip of FIG. 2A, taken along line 2B-2B.

With reference to the drawings, FIGS. 2A and 2B show a test strip 10, in accordance with an exemplary embodiment of the present invention. Test strip 10 can take the form of a substantially flat strip that extends from a proximal end 12 to a distal end 14. In one embodiment, the proximal end 12 of test strip 10 can be narrower than distal end 14 to provide facile visual recognition of distal end 14. For example, test strip 10 may include a tapered section 16, in which the full width of test strip 10 tapers down to proximal end 12, making proximal end 12 narrower than distal end 14. If, for example, a blood sample is applied to an opening in proximal end 12 of test strip 10, providing tapered section 16 and making proximal end 12 narrower than distal end 14 can assist the user in locating the opening where the blood sample is to be applied. Alternatively, the distal end may be tapered. Further, other visual means, such as indicia, notches, contours or the like can be used.

Test strip 10 is depicted in FIGS. 2A and 2B as including a plurality of electrodes 22, 24, 28, 30. Each electrode may extend substantially along the length of test strip 10 to provide an electrical contact near distal end 14 of test strip 10 and a conductive region electrically connecting the region of the electrode near proximal end 12 to the electrical contact. In the exemplary embodiment of FIGS. 2A and 2B, the plurality of electrodes includes a working electrode 22, a counter electrode 24, a fill-detect anode 28, and a fill-detect cathode 30 at a proximal end 12 of test strip 10. Correspondingly, the electrical contacts can include a working electrode contact 32, a counter electrode contact 34, a fill-detect anode contact 36, and a fill-detect cathode contact 38 positioned at distal end 14 of test strip 10. The conductive regions may include a working electrode conductive region 40 that electrically connects the proximal end of working electrode 22 to working electrode contact 32, a counter electrode conductive region 42 that electrically connects the proximal end of counter electrode 24 to counter electrode contact 34, a fill-detect anode conductive region 44 that electrically connects the proximal end of fill-detect anode 28 to fill-detect contact 36, and a fill-detect cathode conductive region 46 that electrically connects the proximal end of fill-detect cathode 30 to fill-detect cathode contact 38.

In one embodiment, at least one electrode is partially housed within a sample chamber to allow contact with a fluid to be tested. For example, FIG. 2B depicts test strip 10 as including a slot 52 that forms a portion of sample chamber 88 at proximal end 12. Slot 52 can define an exposed portion 54 of working electrode 22, an exposed portion 56 of counter electrode 24, an exposed portion 60 of fill-detect anode 28, and an exposed portion 62 of fill-detect cathode 30. Further, the exemplary embodiment includes an auto-on conductor 48 disposed near distal end 14 of strip 10 to allow the meter to determine that a test strip is operatively connected to the meter.

As shown in FIG. 2B, test strip 10 may have a layered construction. Test strip 10 includes a base layer 18 that may substantially extend along the entire length or define the length of test strip 10. Base layer 18 can be formed from an electrically insulating material and can have a thickness sufficient to provide structural support to test strip 10.

According to the exemplary embodiment of FIG. 2B, one or more conductive components 20 may be disposed on at least a portion of base layer 18. Conductive components 20 may include one or more electrically conductive elements, such as, for example, a plurality of electrodes. Conductive components 20 may include any suitable conductive or semi-conductive material, such as, for example, gold, platinum, silver, iridium, carbon, indium tin oxide, indium zinc oxide, copper, aluminum, gallium, iron, mercury amalgams, tantalum, titanium, zirconium, nickel, osmium, rhenium, rhodium, palladium, an organometallic, or a metallic alloy.

Layered on top of base layer 18 and conductive components 20 is a spacer layer 64. Spacer layer 64 may include an electrically insulating material such as polyester. Spacer layer 64 can cover portions of working electrode 22, counter electrode 24, fill-detect anode 28, fill-detect cathode 30, and conductive regions 40-46. In the exemplary embodiment of FIG. 2B spacer layer 64 does not cover electrical contacts 32-38 or auto-on conductor 48. For example, spacer layer 64 can cover a substantial portion of conductive components 20, from a line proximal of contacts 32 and 34 to proximal end 12, except for slot 52 extending from proximal end 12.

A cover 72 may be provided. As shown in FIG. 2B, cover 72 may have a proximal end 74 and a distal end 76 and may be disposed at proximal end 12 of test strip 10 to cover slot 52 thereby partially forming sample chamber 88. Cover 72 can be attached to spacer layer 64 via an adhesive layer 78. Adhesive layer 78 can include a polyacrylic or other adhesive and may include sections disposed on spacer layer 64 on opposite sides of slot 52. In some embodiments, a break 84 in adhesive layer 78 may extend from distal end 70 of slot 52 to an opening 86. It is also contemplated that cover 72 may include one or more openings (not shown) configured to permit venting of sample chamber 88. Cover 72 can be disposed on adhesive layer 78 such that proximal end 74 of cover 72 may be aligned with proximal end 12 and distal end 76 of cover 72 may be aligned with opening 86, thereby covering slot 52 and break 84. Cover 72 may be composed of an electrically insulating material, such as polyester. Additionally, cover 72 may be transparent.

Slot 52, together with base layer 18 and cover 72, may define sample chamber 88 in test strip 10, which receives a fluid sample, such as a blood sample, for measurement in the exemplary embodiment. A proximal end 68 of slot 52 can define a first opening in sample chamber 88, through which the fluid sample is introduced. At distal end 70 of slot 52, break 84 can define a second opening in sample chamber 88, for venting sample chamber 88 as a fluid sample enters sample chamber 88. Slot 52 may be dimensioned such that a blood sample applied to its proximal end 68 is drawn into and held in sample chamber 88 by capillary action, with break 84 venting sample chamber 88 through an opening 86, as the fluid sample enters. Moreover, slot 52 may be dimensioned so that the volume of fluid sample that enters sample chamber 88 by capillary action is about 1 micro-liter or less.

Test strip 10 may include one or more reagent layers 90 disposed in sample chamber 88. In the exemplary embodiment, reagent layer 90 contacts a partially exposed portion 54 of working electrode 22. It is also contemplated that reagent layer 90 may or may not contact exposed portion 56 of counter electrode 24. Reagent layer 90 may include chemical components to enable the level of glucose or other analyte in the body fluid, such as a blood sample, to be determined electro-chemically. For example, reagent layer 90 can include an enzyme specific for glucose, such as glucose oxidase or glucose dehydrogenase, and a mediator, such as potassium ferricyanide or ruthenium hexamine. Reagent layer 90 can also include other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485).

An example of the way in which chemical components of reagent layer 90 may react with glucose in the blood is described next. The glucose oxidase initiates a reaction that oxidizes glucose to gluconic acid and reduces the ferricyanide to ferrocyanide. When an appropriate voltage is applied to working electrode 22, relative to counter electrode 24, the ferrocyanide is oxidized to ferricyanide, thereby generating a current that is related to the glucose concentration in the blood sample.

As depicted in FIG. 2B, the position and dimensions of the layers of test strip 10 may result in test strip 10 having regions of different thicknesses. Of the layers above base layer 18, the thickness of spacer layer 64 may constitute a substantial thickness of test strip 10. Thus the distal end of spacer layer 64 may form a shoulder 92 in test strip 10. Shoulder 92 may delineate a thin section 94 of test strip 10 extending from shoulder 92 to distal end 14, and a thick section 96 of test strip 10 extending from shoulder 92 to proximal end 12. The elements of test strip 10 used to electrically connect it to test meter 200, 208, namely, electrical contacts 32-38 and auto-on conductor 48, can all be located in thin section 94. Accordingly, test meter 200, 208 can be sized and configured to receive thin section 94 but not thick section 96. This may allow the user to insert the correct end of test strip 10, i.e., distal end 14 of thin section 94, and can prevent the user from inserting the wrong end, i.e., proximal end 12 of thick section 96, into test meter 200, 208.

Test strip 10 can be sized for easy handling. For example, test strip 10 may measure approximately 35 mm long (i.e., from proximal end 12 to distal end 14) and about 9 mm wide. According to the exemplary embodiment, base layer 18 may be a polyester material about 0.35 mm thick and spacer layer 64 may be about 0.127 mm thick and cover portions of working electrode 22. Adhesive layer 78 may include a polyacrylic or other adhesive and have a thickness of about 0.013 mm. Cover 72 may be composed of an electrically insulating material, such as polyester, and can have a thickness of about 0.1 mm. Sample chamber 88 can be dimensioned so that the volume of fluid sample held is about 1 micro-liter or less. For example, slot 52 can have a length (i.e., from proximal end 12 to distal end 70) of about 3.56 mm, a width of about 1.52 mm, and a height (which can be substantially defined by the thickness of spacer layer 64) of about 0.13 mm. The dimensions of test strip 10 for suitable use can be readily determined by one of ordinary skill in the art. For example, a meter with automated test strip handling may utilize a test strip smaller than 9 mm wide.

Although FIGS. 2A and 2B show an exemplary embodiment of test strip 10, other configurations, chemical compositions and electrode arrangements could be used. Different arrangements of working electrode 22, counter electrode 24, fill-detect anode 28, and/or fill-detect cathode can also be used. In the configuration shown in FIGS. 2A and 2B, working electrode 22 and counter electrode 24 are separated by boundaries aligned in the x-axis, perpendicular to the length of test strip 10 in the y-axis. Alternatively, working electrode 22 and counter electrode 24 can be separated by boundaries aligned in the y-axis, parallel to the length of test strip 10. It is also contemplated that working electrode 22 and counter electrode 24 may be aligned at any angle relative the length of test strip 10.

Test Strip Array Configuration

Figure 3A:
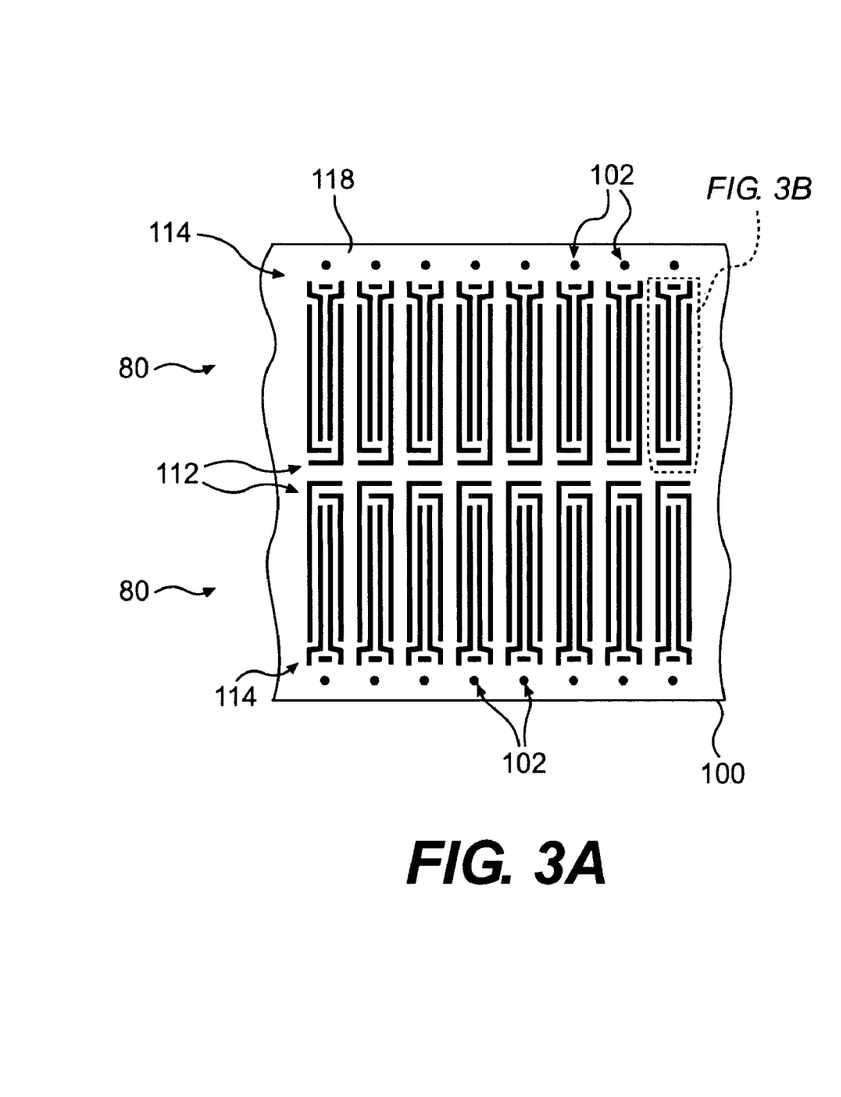
FIG. 3A is a top view of a reel according to an exemplary disclosed embodiment of the invention.

FIG. 3A shows a top view of reel 100 according to an exemplary disclosed embodiment. The term "reel" as used herein applies to a material of continuous indeterminate length or to sheets of material of determinate length. In some embodiments, reel 100 may include base layer 118. As described below, an array of conductive components 120 may be deposited on base layer 118. Various layers may be added to base layer 118 to form test strip 110 similar to that described in FIG. 2B. Test strips 110 may then be separated from the array of test strips 110 formed on reel 100 to produce multiple individual test strips 110.

A plurality of feature sets 80 may be formed on base layer 118, wherein each feature set 80 may include a plurality of conductive components 20, such as, for example, an electrode, a conductive region and an electrode contact. Feature sets 80 may include any suitable conductive or semi-conductive material. In some embodiments, feature sets 80 can be formed using lift-off lithography or shadow masking, as described below.

Figure 3B:
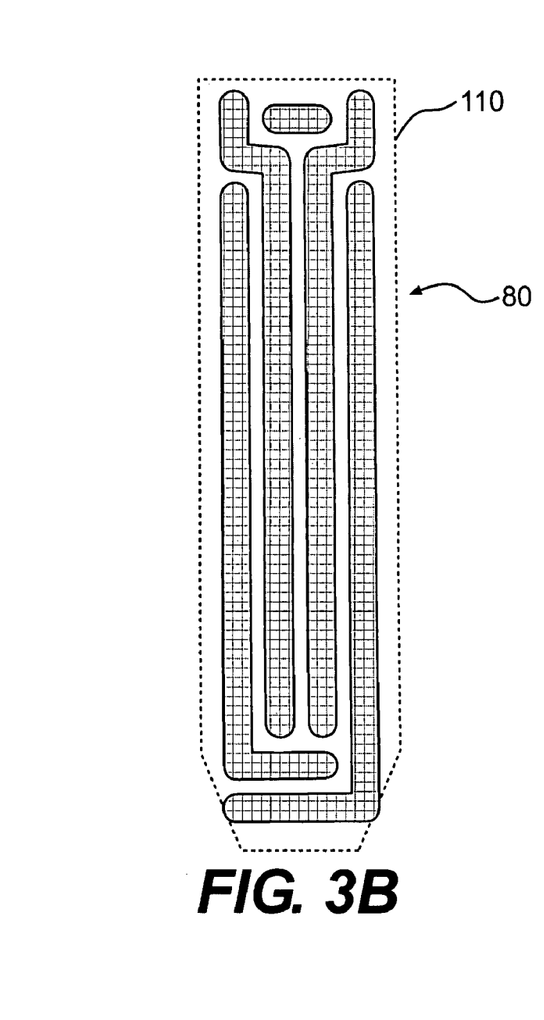
FIG. 3B is an enlarged tip view of a feature set on the reel of FIG. 3A.

Following the formation of one or more feature sets 80 on base layer 118, various layers may be added to base layer 118 and feature sets 80 to form a laminate structure as shown in FIG. 2B. Then, individual test strips 110 may be separated from reel 100 via a "singulation" process, wherein the outer shape of test strip 110 formed by the manufacturing process may be represented by the dotted line shown in FIGS. 3A and 3B. In some embodiments, a single feature set 80 may include conductive components 20 of a single test strip 110. Although FIGS. 3A and 3B shows one configuration of feature set 80, it is understood that other configurations of feature set 80 may be used to form test strip 110.

As shown in FIG. 3A, feature sets 80 may be arranged in two rows on reel 100. In the exemplary embodiment depicted, proximal ends 112 of the two rows of feature sets 80 are in juxtaposition in the center of reel 100 and distal ends 114 of feature sets 80 are arranged at the periphery of reel 100. It is also contemplated that proximal ends 112 and distal ends 114 of feature sets 80 can be arranged in the center of reel 100, and distal ends 114 of two rows of feature sets 80 can be arranged in the center of reel 100. Further, the separation distance between feature sets 80 may be designed to permit a single cut to separate adjacent feature sets 80 during a singulation process.

As shown in FIG. 3A, reel 100 includes a plurality of registration points 102 at the distal end 114 of each test strip on reel 100. Registration points 102 may be used during one or more manufacturing processes to locate a feature of test strip 110 relative to reel 100. One or more manufacturing steps may require registration points 102 to ensure precise alignment of laminate layers and/or other manufacturing processes, such as, for example, deposition of conductive components, mask alignment, reagent deposition, singulation, etc. For example, registration points 102 may be used during lamination to ensure that spacer layer 64 is properly positioned over base layer 18 such that slot 52 is positioned to adequately expose portions of electrodes 54, 56, 60, 62 as shown in FIGS. 2A and 2B. Registration points 102 may also be utilized during chemistry deposition, singulation or any other process associated with the formation of test strips 110.

Registration points 102 may include any suitable reference marks, such as, for example, holes, notches, indentations, raised regions or any other suitable reference indication known in the art. Registration points 102 may be formed by any suitable manufacturing process, such as, for example, laser ablation, stamping, physical deformation, etching, drilling, printing, punching, scoring, heating, compression molding, etc. Further, registration points 102 may be formed at any stage during the formation and/or processing of reel 100. For example, registration points 102 may be formed during the formation of base layer 118 wherein registration points 102 may be formed at regular intervals along base layer 118. In some embodiments, registration points 102 may be formed during the formation of feature sets 80. In particular, registration points 102 may be formed on base layer 118 prior to using lift-off lithography or shadow masking techniques to form feature sets 80 as described below, wherein the position of feature sets 80 on base layer 118 may be dependent upon the position of registration points 102 on base layer 118. In some embodiments a visual system (not shown) may be used to ensure adequate positioning of the formation of feature sets 80 relative to registration points 102. It is also contemplated that additional registration points 102 may be formed, such as, for example, a scribe line (not shown) that may be used during a subsequent manufacturing process, such as, for example, singulation.

Registration points 102 may be located at any suitable location on reel 100. As shown in FIG. 3A, registration points 102 may be located adjacent distal end 114 of each feature set 80. Registration points 102 may also be located at positions other than distal end 114 of each feature set 80, such as, for example, adjacent to proximal end 112 of feature set 80. As feature sets 80 may be located on reel 100 in various patterns and various densities, so to may registration points 102 be appropriately located. For example, it may be appropriate to position registration points 102 between feature sets 80.

Registration point 102 may be distributed at any suitable density on reel 100. In addition, registration points 102 may be distributed on reel 100 at a density different than the density of feature sets 80 on reel 100. For example, the number of registration points 102 distributed within a select region of reel 100 may be different than the number of feature sets 80 distributed within the select region of reel 100. In some embodiments, there may be one registration point for every feature set, and in other embodiments there may be one registration point for every five, ten, or twenty features sets. It is also contemplated that registration points 102 may be separated by different distances or distributed at different densities than feature sets 80 on reel 100. The distribution of feature sets 80 and/or registration points 102 may depend on one or more characteristics of the manufacturing process used to produce test strip 10 and/or the design of test strip 10.

Manufacturing of Test Strips

Figure 4A:
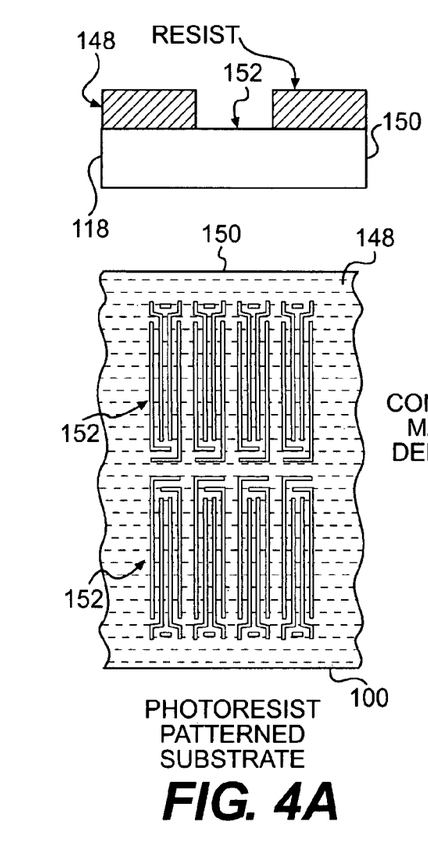
FIG. 4A is a cross-sectional view and a top view of a structure that illustrate a method for manufacturing a test strip using a lift-off lithography process, according to an exemplary disclosed embodiment.
Figure 4B:
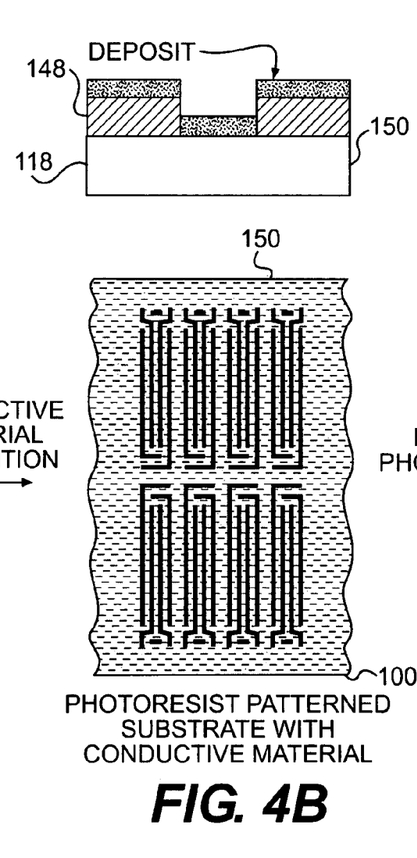
FIG. 4B is a cross-sectional view and a top view of the structure of FIG. 4A illustrating a method for manufacturing the test strip using lift-off lithography process, according to the exemplary disclosed embodiment.

FIGS. 4A-4E illustrate a method for manufacturing a test strip 110 using a lift-off lithography process, according to an exemplary disclosed embodiment. Lithography typically includes the formation of a pattern in a photosensitive material by the selective exposure of radiation to the patterned region of the photosensitive material. Photosensitive material may include any suitable material that may change a property upon exposure to radiation, such as, visible light or ultraviolet radiation. Exposure of a photosensitive material to radiation can affect a property of the exposed and unexposed regions differently. For example, a property affected by radiation may include chemical resistance, wherein the photosensitive material may be referred to as a photoresist. A photoresist material may exhibit differential resistance to chemical etching whereby regions of the photoresist exposed to radiation may be degraded by a chemical, and regions unexposed to radiation may resist chemical degradation. Such a process is known in the art and may be used to form a photoresist patterned substrate 150 as shown in FIGS. 4A and 4B. Specifically, a photoresist layer 148 may be formed on base layer 118 using any suitable lithographic process known in the art.

Photoresist layer 148 may include any suitable photoresist material. For example, photoresist layer 148 may include Shipley's 1805™, Shipley's 1813™, Shipley's 1818™, Shipley's 1045™, Shipley's 1075™, AZ's 9260™, or Futurex™. Other suitable materials may be used, and photoresist layer 148 may be deposited on base layer 118 using any suitable method known in the art.

Figure 4C:
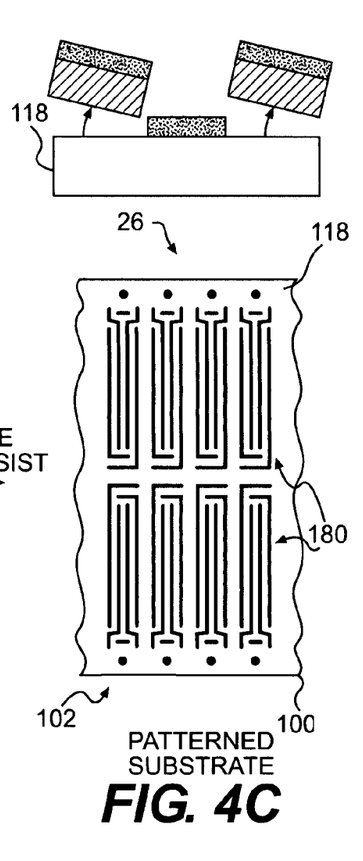
FIG. 4C is a cross-sectional view and a top view of the structure of FIG. 4B illustrating a method for manufacturing the test strip using lift-off lithography process, according to the exemplary disclosed embodiment.

Following deposition of photoresist layer 148 on base layer 118, lithography procedures can be used to produce a pattern 152 in photoresist layer 148, as shown in FIG. 4A, wherein pattern 152 may form an array of feature sets 180, as shown in FIG. 4C. For example, a mask (not shown) containing pattern 152 may be placed over photoresist layer 148. The mask and photoresist layer 148 may then be irradiated with UV light to selectively alter a chemical property of the exposed region of photoresist layer 148. Alternatively, a laser (not shown) may be used to irradiate pattern 152 onto photoresist layer 148 such that no mask is required. Following selective exposure of photoresist layer 148 to radiation, a chemical may be applied to preferentially degrade exposed regions of photoresist layer 148 to form a photoresist patterned substrate 150.

Following formation of photoresist patterned substrate 150, a conductive material may be applied to photoresist patterned substrate 150 using a conductive material deposition method as shown in FIG. 4B. Conductive material may include any conductive or semi-conductive material, such as, for example, palladium, gold, platinum, silver, iridium, carbon, indium tin oxide, indium zinc oxide, copper, aluminum, gallium, iron, mercury amalgams, tantalum, titanium, zirconium, nickel, osmium, rhenium, rhodium, palladium, an organometallic, or a metallic alloy.

Conductive material deposition methods may include any suitable method, such as, for example, physical vapor deposition, chemical vapor deposition, electroplating, or spray techniques. Physical vapor deposition may include sputtering, wherein vaporized ions of conductive material are directed onto photoresist patterned substrate 150. Physical vapor deposition may also include evaporation, wherein a conductive material is heated in a vacuum to release particles that can condense onto photoresist patterned substrate 150.

Electroplating may include placing photoresist patterned substrate 150 in a liquid solution and applying a potential to form conductive material on photoresist patterned substrate 150. Spraying may include ultrasonic or pressure spraying and usually involves the deposition of a liquid form metal ink, typically an organometallic. The organic components may be sprayed onto photoresist patterned substrate 150 to form a uniform conductive layer, and the substrate and conductive layer may be baked to remove organic solvents and binders.

In some embodiments, a bonding layer (not shown) may be deposited on base layer 118 before forming feature sets 180 on base layer 118. In particular, the bonding layer may be configured to enhance a bond strength between base layer 118 and the conductive material by providing stronger adhesion between the conductive material and the bonding layer than base layer 118 and the conductive material. For example, a bonding layer of titanium or chromium may be deposited on base layer 118 before depositing the conductive material on base layer 118.

As shown in FIG. 4C, following a conductive material deposition process, photoresist layer 148 may be removed. Specifically, photoresist layer 148 may be removed from base layer 118 by any suitable removal process, such as, for example, using a liquid or a gas solvent. Various solvents may be used to remove photoresist layer 148, such as, for example, a Shipley brand stripper, acetone, trichloroethylene, methyl ethyl ketone, or methyl isobutyl ketone. The removal of photoresist layer 148 may preferentially remove photoresist layer 148 while not substantially removing conductive material selectively deposited on base layer 118. Removal of photoresist layer 148 may expose conductive material deposited on base layer 118 through pattern 152, such as, for example, feature sets 80.

Figure 4D:
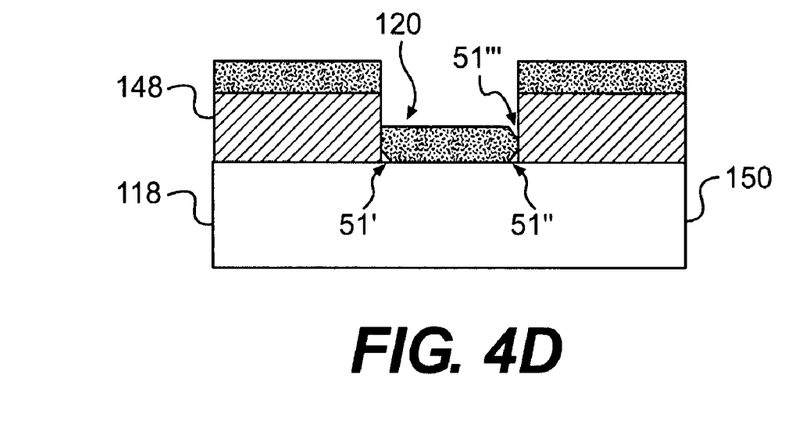
FIG. 4D is an enlarged view of a cross-section of the structure shown by FIGS. 4B and 4C, illustrating a method for manufacturing the test strip using lift-off lithography process, according to the exemplary disclosed embodiment.

FIG. 4D illustrates an enlarged view of cross-sections of the structures shown by FIGS. 4B and 4C, illustrating a method for manufacturing test strip 110 using the lift-off lithography process. In some embodiments, a wall feature 51 may be formed by a manufacturing process utilizing lift-off lithography and/or a shadow mask as described below. Wall feature 51 may include an indentation or similar structure formed on the wall of one or more conductive components 120. For example, wall feature 51 may include a shoulder or bevel at least partially extending along a wall of conductive components 120.

Figure 4E:
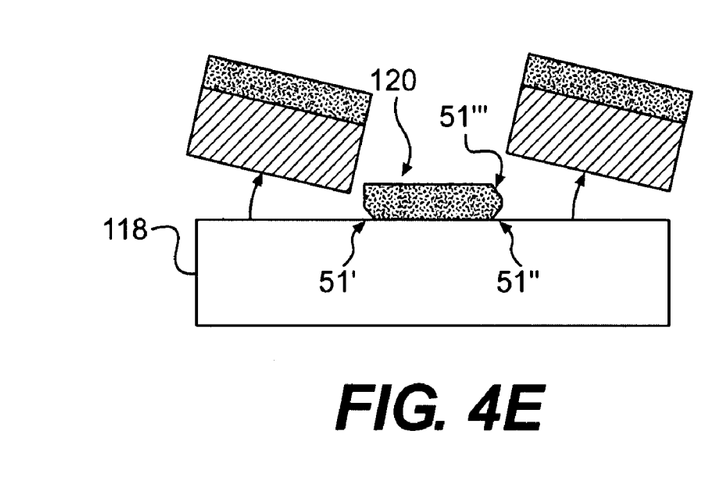
FIG. 4E is an enlarged view of a cross-section of the structure shown by FIGS. 4B and 4C, illustrating a method for manufacturing the test strip using lift-off lithography process, according to the exemplary disclosed embodiment.

One or more wall features 51 may result from a sputtering process. In particular, deposition of conductive material on base layer 118 through photoresist layer 148 may not result in complete deposition of conductive material in regions adjacent to intersections between base layer 118 and photoresist layer 148. For example, as shown in FIGS. 4D and 4E, wall features 51', 51" may form at regions at the bottom of conductive component 120 as conductive material deposited on base layer 118 may not fill the entire region enclosed by photoresist 148.

In some embodiments, wall features 51 may be formed in any wall region of conductive components 120. For example, as shown in FIGS. 4D and 4E wall feature 51''' may be formed at a top region of conductive component 120. Wall feature 51''' may be formed by sputtering conductive material at a suitable trajectory toward photoresist patterned substrate 150, or any other method known in the art. It is also contemplated that photoresist layer 148 may include one or more structures representing a mold of wall feature 51, such that conductive material may form in, or around, the mold to form wall feature 51. For example, wall feature 51 may include a protrusion in a wall of conductive components 120 formed by depositing conductive material in an indentation in a wall of photoresist layer 148.

Figure 5A:
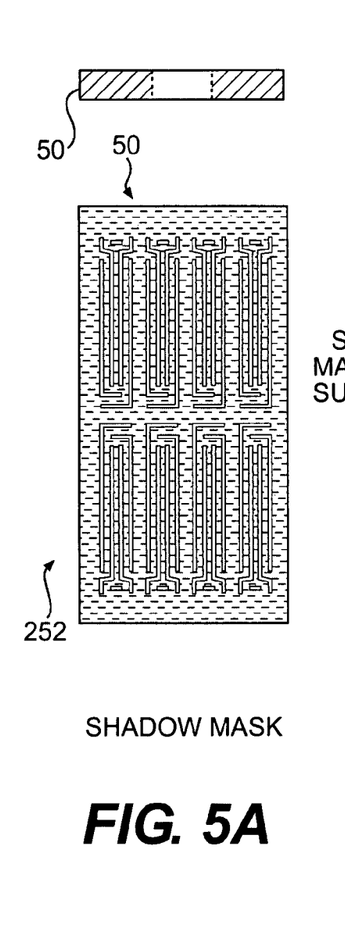
FIG. 5A is a cross-sectional view and a top view of a shadow mask, according to an exemplary disclosed embodiment.
Figure 5B:
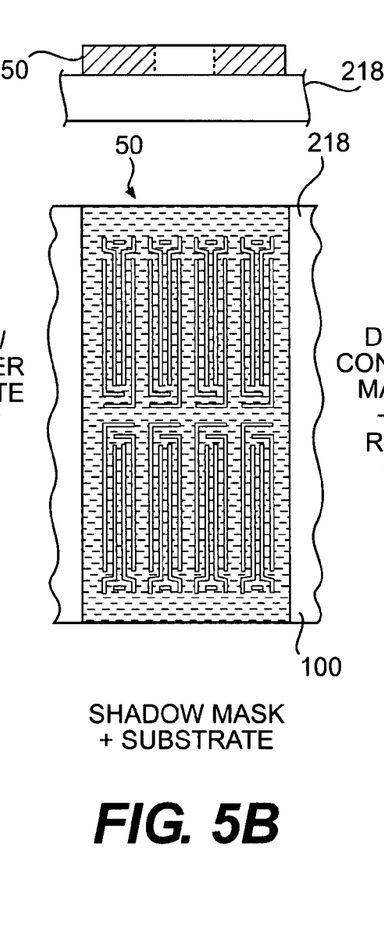
FIG. 5B is a cross-sectional view and a top view of the shadow mask of FIG. 5A illustrating a method for manufacturing a test strip using the shadow mask, according to an exemplary disclosed embodiment.
Figure 5C:
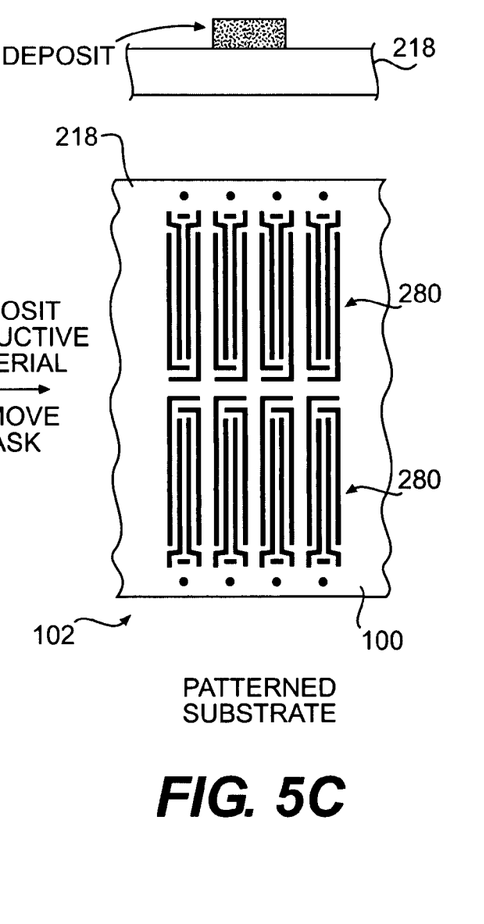
FIG. 5C is a cross-sectional view and a top view of the structure of FIG. 5B illustrating a method for manufacturing the test strip using the shadow mask, according to an exemplary disclosed embodiment.

FIGS. 5A-5C illustrate a method for test strip manufacturing using a shadow mask 50, according to an exemplary disclosed embodiment. Specifically, shadow mask 50 (see FIG. 5A) may be used to form one or more feature sets 280 on base layer 218, wherein shadow mask 50 may contain pattern 252 of feature sets 280. Shadow mask 50 may be produced by any method known in the art, such as, for example, by a photo-etching process, an electroforming, or an etching process. Shadow mask 50 may be made of any suitable material, such as, for example, molybdenum, aluminum, nickel, silicon or a polymer such as polyethylene terephthalate. Shadow mask 50 may be placed over and maintained in close contact with base layer 218 using any techniques known in the art.

As shown in FIG. 5A-5C, following suitable placement of shadow mask 50 over base layer 218, a conductive material may be deposited on base layer 218 as described previously with reference to FIGS. 4A-4C. Specifically, the conductive material may be deposited such that conductive material may be formed on base layer 218 by passing conductive material through shadow mask 50. In particular, the conductive material may be deposited to form feature sets 280 by passing conductive material through pattern 252 of shadow mask 50.

As shown in FIG. 5C, shadow mask 50 may be removed from base layer 218 following deposition of the conductive material. Shadow mask 50 may be removed using methods known in the art, such as, for example, peeling shadow mask off base layer 218 or use of appropriate solvents. Following removal of shadow mask 50, reel 100 may be prepared for further manufacturing. As described above, it is also contemplated that feature sets 280 may include one or more wall features 51 (not shown). Wall features 51 may arise from the deposition of conductive material on base layer 218 passing through shadow mask 50, or may be formed if shadow mask 50 includes one or more structures representing a mold of wall feature 51.

Shadow mask 50 and/or reel 100 may be configured to permit consistent production of high quality feature sets 280. In particular, shadow mask 50 and/or reel 100 may be configured to permit formation of feature sets 280 at a selected density and resolution. For example, shadow mask 50 may be maintained in close contact with base layer 218 to minimize the likelihood that deposited conductive material may flow between shadow mask 50 and base layer 218. In addition, shadow mask 50 may include an adhesive material (not shown), such as, for example, a pressure sensitive adhesive and/or a heat activated adhesive. The adhesive material may enhance the manufacturing process by providing removable bonding between shadow mask 50 and base layer 218. It is also contemplated that other methods may be used to maintain suitable contact between shadow mask 50 and base layer 218, such as, for example, use of magnets.

Figure 6:
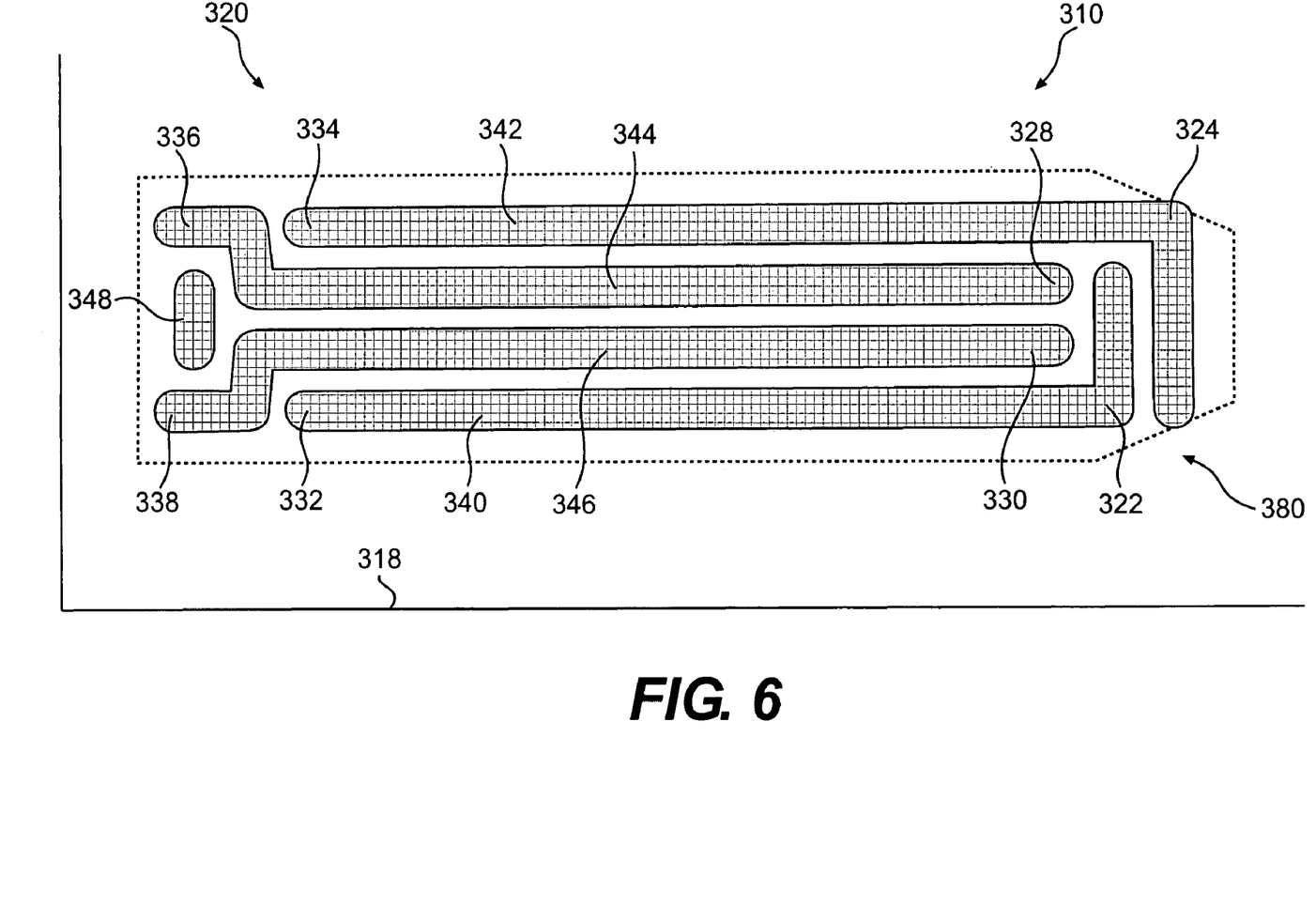
FIG. 6 is a top view of a conductive base layer of a test strip according to an exemplary embodiment of the invention.
Figure 7:
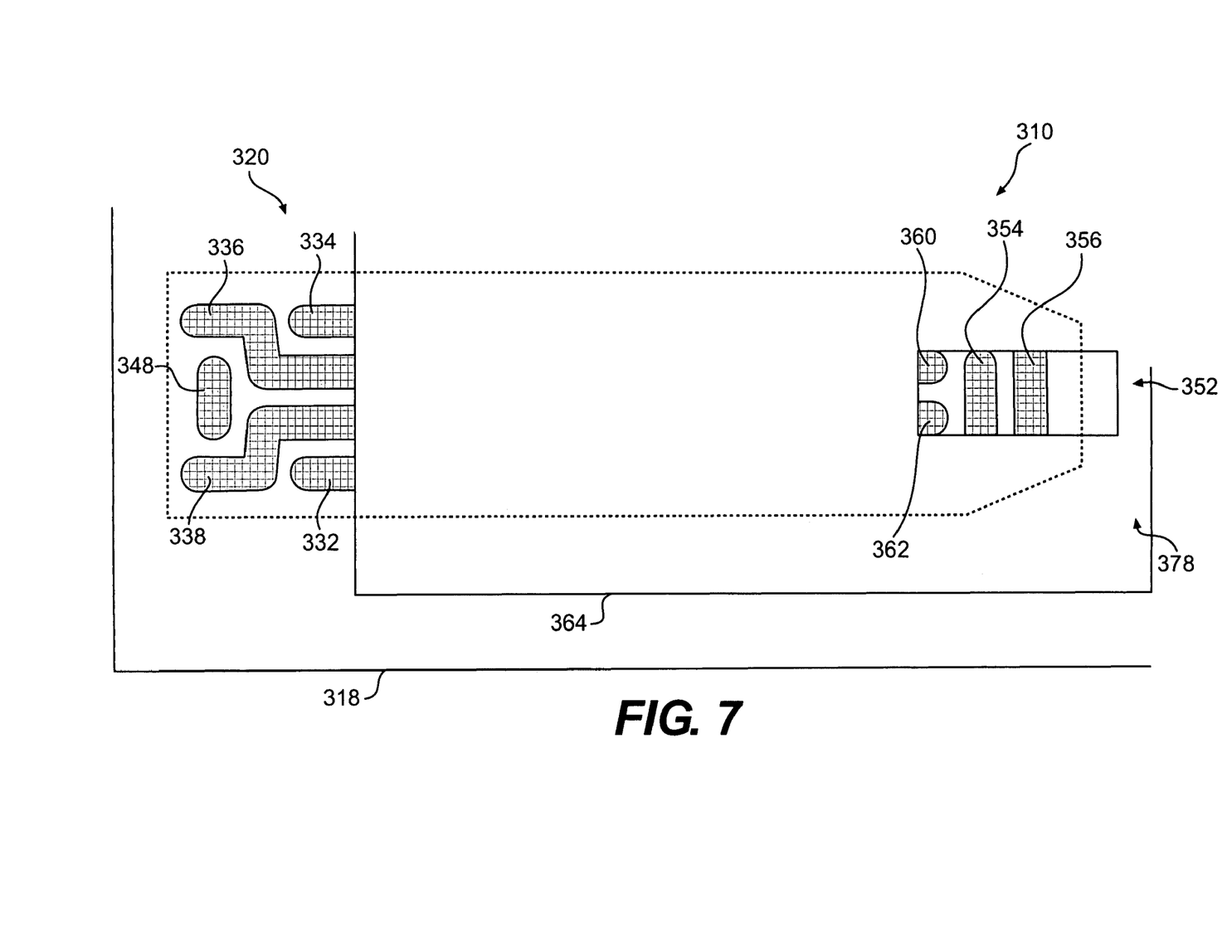
FIG. 7 is a top view of a dielectric layer of a test strip according to an exemplary embodiment of the invention.

FIGS. 6 and 7 show a partially fabricated test strip structure 310 that may be fabricated according to the process described with respect to FIGS. 4A-4E and 5A-5C. In each of FIGS. 6 and 7, the outer shape of the test strip 310 that would be formed in the overall manufacturing process is shown as a dotted line. Although these figures show steps for manufacturing test strip 310 with a configuration similar to that shown in FIGS. 1A, 2A, 2B, it is to be understood that similar steps can be used to manufacture test strips having other configurations of components.

As depicted in the exemplary embodiment shown in FIG. 6, test strip 310 may include a plurality of conductive components 320, such as, for example, electrodes 322, 324, 328 and 330. Conductive components 320 of test strip 310 may be partially formed by forming feature set 380 as discussed above. In some embodiments, conductive components 320 may be at least partially formed by one or more processing techniques. For example, a processing technique, such as laser ablation, may be used to more precisely define the boundaries of some conductive components 320. In other embodiments, a processing technique may include lamination, etching or a physical separation process, such as, for example, stamping and cutting.

Test strip 310 may also include one or more coding regions (not shown), configured to provide coding information on test strip 310. For example, coding regions may include a discrete set of contacting pads as described in commonly-assigned, copending patent application "DIAGNOSTIC STRIP CODING SYSTEM AND RELATED METHODS OF USE", filed Jul. 15, 2005 (Attorney Docket 06882-0147), the disclosures of which is hereby incorporated herein by reference in its entirety. The discrete pattern formed by a set of contacting pads may include conducting and non-conducting regions designed to be readable by test meter to identify data particular to the test strip.

Following the formation of feature set 380 on base layer 318, spacer layer 364 can be applied to conductive components 320 and base layer 318, as illustrated in FIG. 7. Spacer layer 364 can be applied to conductive components 320 and base layer 318 in a number of different ways. In an exemplary approach, spacer layer 364 may be provided as a sheet or web large enough and appropriately shaped to cover multiple feature sets 380. In this approach, the underside of spacer layer 364 can be coated with an adhesive to facilitate attachment to conductive components 320 and base layer 318. Various slots can be cut, formed or punched out of spacer layer 364 to shape it before, during or after the application of spacer layer 364 to conductive components 320. For example, as shown in FIG. 7, spacer layer 364 can have a pre-formed slot 352 for each test strip structure. Spacer layer 364 may be positioned over conductive components 320, as shown in FIG. 7, and laminated to conductive components 320 and base layer 318. When spacer layer 364 is appropriately positioned on conductive components 320, exposed electrode portions 354-362 are accessible through slot 352. Similarly, spacer layer 364 leaves contacts 332-338 and auto-on conductor 348 exposed after lamination.

Alternatively, spacer layer 364 could be applied in other ways. For example, spacer layer 64 can be injection molded onto base layer 318 and conductive components 320. Spacer layer 64 could also be built up on base layer 318 and conductive components 320 by screen-printing successive layers of a dielectric material to an appropriate thickness, e.g., about 0.005 inches. An exemplary dielectric material comprises a mixture of silicone and acrylic compounds, such as the "Membrane Switch Composition 5018" available from E.I. DuPont de Nemours & Co., Wilmington, Del. Other materials also could be used, however.

Reagent layer 390 (not shown) can then be applied to each test strip structure after forming spacer layer 364. In an exemplary approach, reagent layer 390 may be applied by micropipetting an aqueous composition onto exposed portion 354 of working electrode 322 and letting it dry to form reagent layer 390. It is also contemplated that reagent layer 390 may or may not contact exposed portion 356 of counter electrode 324. An exemplary aqueous composition has a pH of about 7.5 and contains 175 mM ruthenium hexamine, 75 mM potassium phosphate, 0.35% Methocel, 0.08% Triton X-100, 5000 u/mL glucose dehydrogenase, 5% sucrose, and 0.05% Silwet. Alternatively, other methods, such as screen-printing, spray deposition, piezo and ink jet printing, can be used to apply the composition used to form reagent layer 390.

Cover 372 (not shown) can then be attached to spacer layer 364, where cover 372 is constructed to cover slot 352, as previously described with respect to FIG. 2B. In some embodiments, one or more registration points 102 may be used to facilitate alignment of cover 372, spacer layer 364, and/or base layer 318. Further, portions of the upper surface of spacer layer 364 can also be coated with an adhesive in order to provide adhesive layer 378 to adhere to cover 372. It is also contemplated that cover 372 can include adhesive layer 378 (not shown) configured to adhere to spacer layer 364. Following attachment of cover 372, individual test strips 310 may be separated from the laminated reel. In an exemplary embodiment, the separation process may include stamping or "punching out" individual test strips 310 in a singulation process.

Preferred embodiments of the present invention have been described above. Those skilled in the art will understand, however, that changes and modifications may be made to these embodiments without departing from the true scope and spirit of the invention, which is defined by the claims.

What is claimed is:

1. A method for manufacturing a biosensor, comprising: providing a laminate structure including a substantially planar base layer containing a plurality of registration points and a photoresist layer containing a pattern of a plurality of feature sets; forming at least one of the plurality of feature sets on the substantially planar base layer by selectively depositing a layer of a conductive material on the substantially planar base layer by passing the conductive material through the pattern of the photoresist layer; and removing the photoresist layer from the substantially planar base layer.

2. The method of claim 1, wherein the photoresist layer includes at least one of Shipley's 1705, Shipley's 1713, Shipley's 1717, Shipley's 1045, Shipley's 1075, AZ's 9260, and Futurex.

3. The method of claim 1, wherein at least one of the plurality of feature sets includes at least one of a working electrode, a counter electrode, a fill-detect electrode, an auto-on conductor, and a coding region.

4. The method of claim 1, wherein the plurality of registration points are formed by at least one of laser ablation, etching, drilling, printing, punching, scoring, heating, compression and molding.

5. The method of claim 1, wherein the plurality of feature sets formed on the substantially planar base layer are separated by less than 10 mm.

6. The method of claim 1, wherein the plurality of registration points are separated by less than 500 mm.

7. The method of claim 1, wherein the plurality of feature sets formed on the substantially planar base layer are formed at a density greater than one per 400 $mm^2$.

8. The method of claim 1, wherein the plurality of feature sets formed on the substantially planar base layer are formed at a density greater than a density of the plurality of registration points on the substantially planar base layer.

9. The method of claim 1, wherein at least one of the plurality of feature sets is less than 40 mm in length.

10. The method of claim 1, wherein at least one of the plurality of registration points is less than 10 mm wide.

11. The method of claim 1, wherein removing the photoresist layer includes the use of a solvent.

12. The method of claim 11, wherein the solvent is at least one of a Shipley brand stripper, acetone, trichloroethylene, methyl ethyl ketone, and methyl isobutyl ketone.

13. The method of claim 1, wherein depositing the layer of the conductive material includes at least one of physical vapor deposition, electroplating, ultrasonic spraying and pressure spraying.

14. The method of claim 13, wherein physical vapor deposition includes at lest one of sputtering and evaporation.

15. The method of claim 1, wherein the conductive material includes at least one material selected from the group consisting of gold, platinum, silver, iridium, carbon, indium tin oxide, indium zinc oxide, copper, aluminum, gallium, iron, mercury amalgams, tantalum, titanium, zirconium, nickel, osmium, rhenium, rhodium, palladium, an organometallic, and a metallic alloy.

16. The method of claim 1, wherein the method further includes depositing a bonding layer on the substantially planar base layer before depositing the conductive material on the substantially planar base layer.

17. The method of claim 16, wherein the bonding layer includes at least one of titanium and chromium.

18. The method of claim 1, wherein the method further includes depositing a reagent layer to contact a portion of the plurality of feature sets.

19. The method of claim 18, wherein the reagent layer further includes at least one of glucose oxidase, glucose dehydrogenase, potassium ferricyanide, and ruthenium hexamine.

* * * * *